United States Patent [19]

Seagel et al.

[11] Patent Number: 4,722,371
[45] Date of Patent: Feb. 2, 1988

[54] METABOLISM CONTAINER

[75] Inventors: Graham C. Seagel; William F. A. Duncan, both of North Vancouver, Canada; Mark D. Munn, Pullman, Wash.

[73] Assignee: Reid, Crowther & Partners Ltd., North Vancouver, Canada

[21] Appl. No.: 914,322

[22] Filed: Oct. 2, 1986

[51] Int. Cl.$^4$ .............................................. B65B 3/04
[52] U.S. Cl. ...................................... 141/98; 141/325; 366/142; 422/50; 422/102; 422/174
[58] Field of Search ................... 422/50, 99, 102, 174; 141/98, 325–327; 366/142

[56] References Cited

U.S. PATENT DOCUMENTS 1,320,323 10/1919 Drucker et al. ...................... 422/50

Primary Examiner—Houston S. Bell, Jr.
Attorney, Agent, or Firm—Uren John R.

[57] ABSTRACT

A portable metabolism container for ecological testing. A substantially air and water tight container having continuous inner walls includes a diffuser unit mounted within the container and operated from a portable power source. The diffuser unit is operable to ingest and discharge water within the container and to set up a uniform water velocity simulating natural flow conditions over a substrate placed within the container.

14 Claims, 4 Drawing Figures

METABOLISM CONTAINER

INTRODUCTION

This invention relates to a metabolism container and, more particularly, to a metabolism container used for testing benthic type organisms obtained from or living in a body of water.

BACKGROUND OF THE INVENTION

To measure the health of a stream or other body of water, a highly important index called the P:R or production:respiration ratio using dissolved oxygen as the indicator is used. This ratio provides a measure of the gross production of biomass or carbon by a benthic community. The community oxygen respiration and production is a sensitive indicator of stress on the functioning of the benthic stream community.

To assess the effect of a toxicant or contaminant on the quality of fresh water, single species toxicity tests are commonly used on an organism of interest. Such tests measure the rate of synthesis of organic material and the decomposition of organic material and, while beneficial in enhancing prediction, are deficient in that they do not duplicate the complex interacting relationships inherent in an ecological system. This disadvantage can be overcome to some extent by utilizing information obtained from the actual aquatic environment in which the organism lives. Such measurements are obtained using the "open reach" method in determining dissolved oxygen at two or more points in a stream with the difference in oxygen obtained between the points giving an estimate of benthic metabolism. The open reach method, however, is deficient because of the diffusion of gases along the water surface between the various points and due to the variations in the water body.

Such diffusions led to the development of a wide variety of enclosed containers which were placed within the stream or body of water to measure both production and respiration under conditions more closely resembling those of the natural habitat. The major advantage of such containers is that easy measurement of ambient gaseous conditions may be obtained together with eliminating the gas diffusion problem and other uncontrollable variations arising from different testing locations and different testing times as is inherent in the open reach testing method.

The enclosed containers used to date, however, have suffered from various disadvantages. In one container, the use of an enclosed rectangular cavity caused "dead" spots in the corner areas which were not replicated in a natural environment. In another container, the use of a pump mounted externally from the container required a large power supply that is not readily portable, portability being a desirable attribute of such containers. In another container, no flow of water was provided within the container over the substrate. Rather, a mere mixing was done which did not simulate flow conditions such as occur in the natural environment. In yet another container, the flow of water within the container over the substrate was not uniform but, rather, was highly uneven. This, again, did not allow replication of conditions identifiable with the natural state or environment conditions surrounding the benthic substrate.

SUMMARY OF THE INVENTION

According to one aspect of the present invention, there is disclosed a metabolism container for ecological testing comprising a substantially air and water tight chamber, a water diffuser means mounted within said chamber, a power source for said water diffuser means and access means to said chamber, said water diffuser means being operable to substantially uniformly propel said water within said chamber at a relatively constant velocity.

According to a further aspect of the invention, there is disclosed water diffuser apparatus comprising a cylinder, a propeller, and a power source for said propeller mounted within said cylinder, a water intake opening on the periphery of said cylinder adjacent to and upstream of said propeller and a water egress opening extending in a decreasing cross-sectional area along said periphery of said cylinder from a position adjacent to and downstream of said propeller to a position at the far end of said cylinder, said water egress opening being located on the opposite side of said cylinder from said water intake opening.

BRIEF DESCRIPTION OF THE SEVERAL VIEWS OF THE DRAWINGS

A specific embodiment of the invention will now be described, by way of example only, with reference to the accompanying drawings in which.

DESCRIPTION OF SPECIFIC EMBODIMENT

Figure 1:
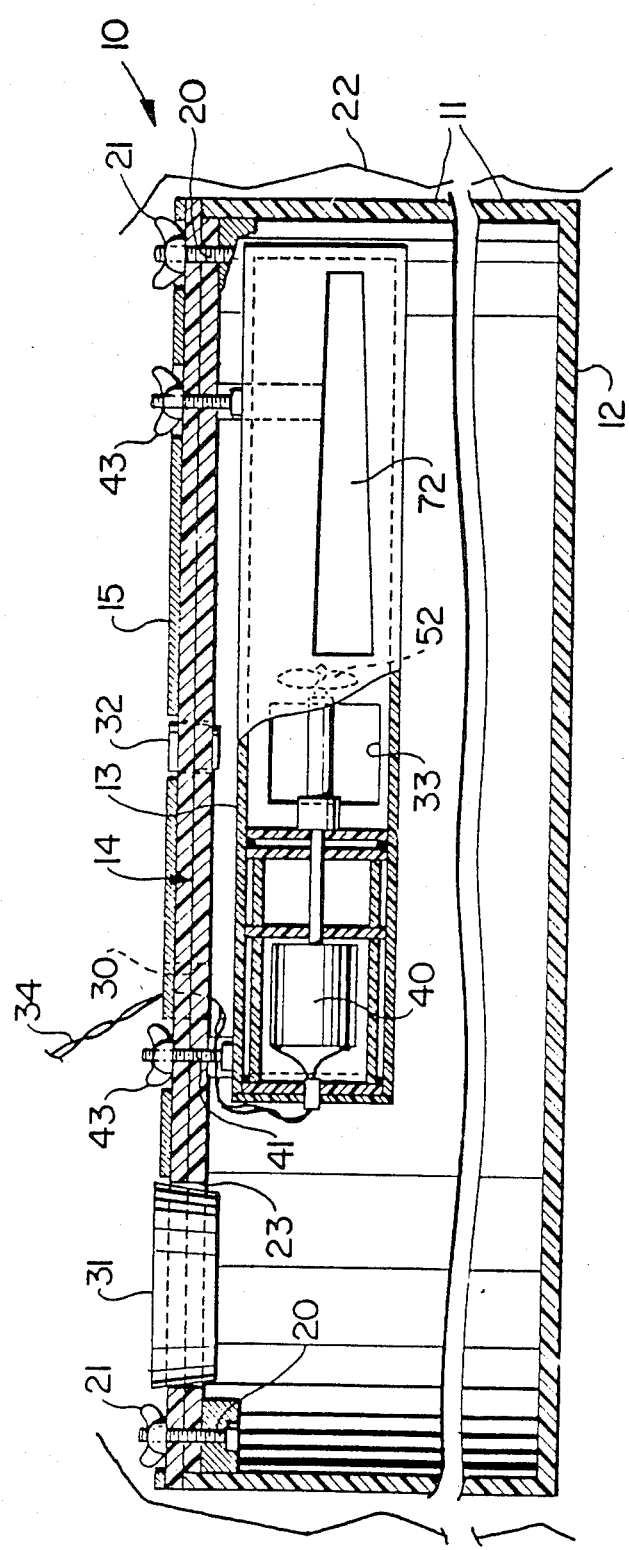
FIG. 1 is a cutaway side view of the metabolism chamber according to the invention with a blackout curtain mounted thereon.

With reference to the drawings, a metabolism container according to the invention is illustrated generally at 10 in FIG. 1. It comprises a base unit or chamber 11 in cylindrical form with a substantially unbroken inner circumference with a bottom closure member 12, a diffuser unit 13 and a lid member 14 connected to the chamber 11 with bolts 20 and accompanying wing nuts 21. A blackout curtain or cover 22 is connected to a blackout lid 15 which is positioned on top of the lid member 14. The blackout curtain 22 may be moved vertically upwardly or downwardly about the chamber 11 to allow more or less light to be exposed to the chamber 11. All of the non-metallic parts of the metabolism container 10 with the exception of the blackout curtain 22 are of transparent plastic to allow unimpeded observation.

Figure 2B:
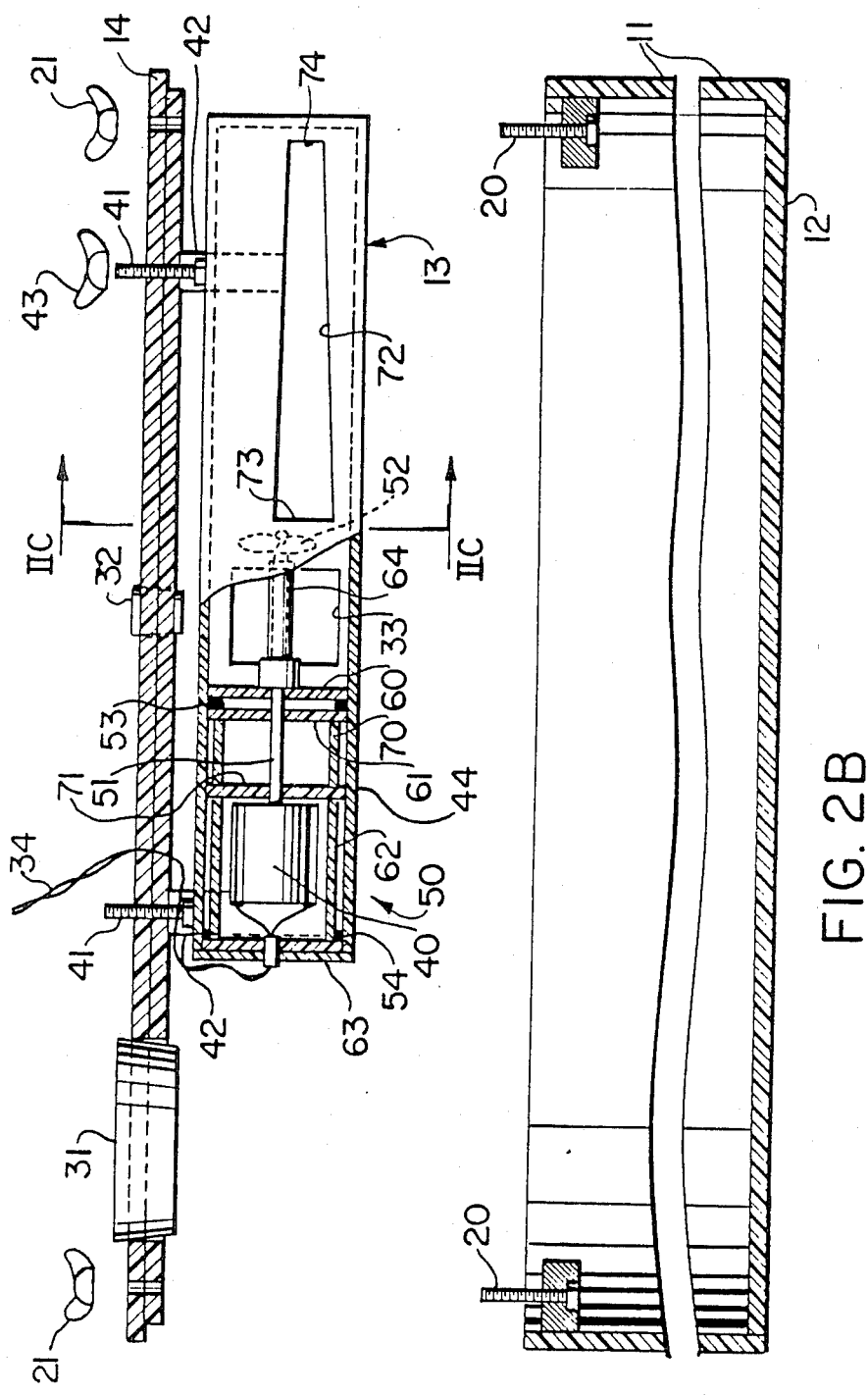
FIG. 2B is a semi-exploded view of the metabolism chamber of FIG. 2A.
Figure 2A:
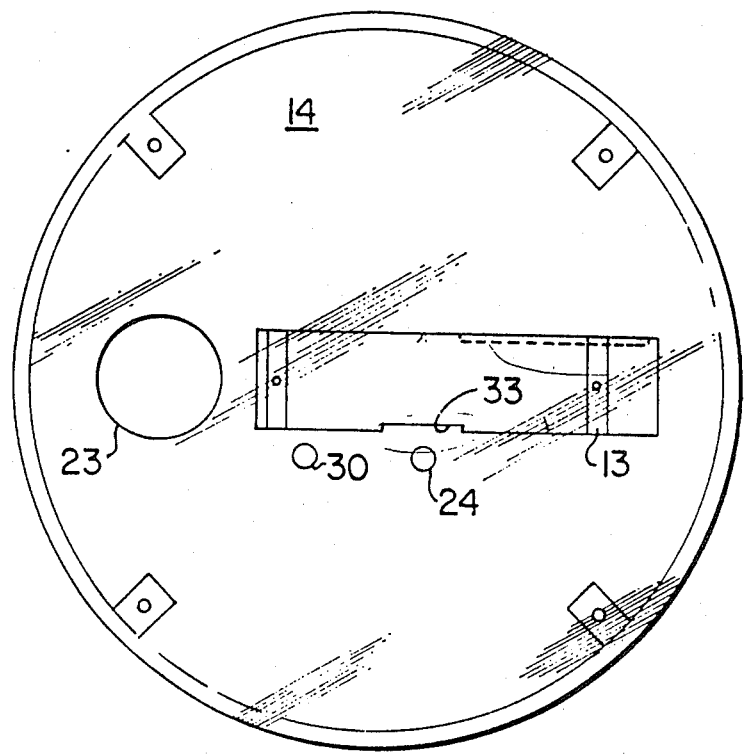
FIG. 2A is a diagrammatic plan view of the metabolism chamber of FIG. 1 without the blackout curtain.
Figure 2C:
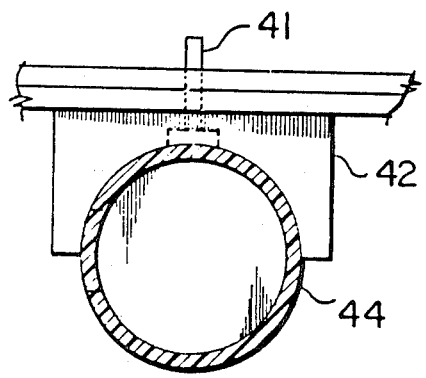
FIG. 2C is a view taken along C—C of FIG. 2B.

The lid member 14 and blackout lid 15 when installed have three access ports 23, 24, 30 (FIG. 2A). Access port 23, shown sealed with a rubber stopper 31, is used for inserting an oxygen probe (not shown) to obtain information on the ambient oxygen present in the water in the metabolism container 10. Many other probes could be used here instead of or in addition to the oxygen probe. Other probes commonly used could include probes indicating water temperature, carbon dioxide, water ph, water turbidity or conductivity and specific ion probes. The location of the access opening is of interest as it is in an area of the flow which is relatively uniform and well mixed.

Access port 24, shown sealed with resealable serum type stopper 32, is used to inject a substance to the water carried in the chamber 11 or to remove a water sample for analysis. Its location is such that any injected substance entering the water through the access port 24 is quickly dispersed because of its position adjacent to the intake opening 33 of the diffuser unit 13 as will be described in greater detail hereafter.

Access port 30 is intended to allow the power supply connections 34 to pass from the motor 40 within diffuser unit 13 to a portable battery pack (not illustrated). The battery pack used may be submersible if it is intended to be positioned with the metabolism container 11 in its operating position.

The diffuser unit 13 is illustrated more clearly in FIG. 2B. It is connected to the lid member 14 with bolts 41 connected between brackets 42 and wing nuts 43. Brackets 42 are connected to the cylinder 44 of the diffuser unit 13 and retain it in its operating position extending downwardly from lid member 14. The diffuser unit 13 is mounted so as to closely coincide with a diameter of the chamber 11.

A mixing unit generally illustrated at 50 comprises the aforementioned motor 40 connected through propeller tailshaft 51 to propeller 52. Aforementioned power supply connection 34 extends from the motor 40 to a power source (not illustrated). Motor 40 is a relatively small D.C. motor and it turns the propeller 52 at one of two available steady revolution rates to enable mixing and fluid flow to occur in the chamber 11. The two revolution rates are provided by the motor 40 being powered by either a 1.5 volt or 3.0 volt power supply.

The mixing unit 50 is mounted in the cylinder 44 of the diffuser unit 13 using O-rings 53, 54. O-ring 53 is positioned between the cylinder 44 and bulkheads 60, 61 and O-ring 54 is positioned between the mixing unit holding cylinder 62 and the cylinder 44. Thus, the mixing unit 50 is removable as a unit from cylinder 44 by removing press-on end diameter 63 and, when inserted in the cylinder, the area between O-rings 53, 54 is water and airtight.

The propeller shaft 51 is mounted within a tube 64, the tube 64 extending through both bulkheads 60, 61 and the circumferential space between the tube 64 and the propeller shaft 51 being open to the water in the chamber 11 and diffuser unit 13. A circumferential hole 70 is drilled in the bottom area of the mixing unit holding cylinder 62 between bulkhead 61 and bulkhead 71. Thus, as water enters tube 64 around propeller shaft 51, it may pass through tube 64 into the area between bulkheads 61, 71 and pass through hole 70. As the air in the mixing unit 50 is displaced by the entering water, it increases in pressure until a steady state amount of water enters the mixing unit, which amount is well below the outside of motor 40 to avoid immersion problems.

The diffuser unit 13 has intake or ingress opening 33 and egress opening 72 located on opposite sides of the cylinder 44. Intake opening 33 is located upstream of the propeller 52 on a first side of the cylinder 44 relatively close to the axis of the metabolism chamber 10. Exit or egress opening 72 is located downstream of the propeller 52 and extends along the cylinder 13 in a trapezoidal configuration of decreasing area from its position 73 closest to the propeller 52 to its position 74 furthest removed from the propeller 52. The configuration of the egress opening 72 is intended to compensate for the increasing pressure head as the end of cylinder 13 is approached. By allowing more water to escape at the initial or closest position of the opening 72 to the propeller 52, the force exerted by the escaping water is more nearly constant than would be the case if the opening 72 were of a constant width.

OPERATION

In operation, it will be first assumed that the metabolism chamber 10 is to be submersed in a stream or river and that the specimen or benthic substrate is to be added to the chamber 11. The container 10 is then submerged in the water and, when it is full of water, the lid member 14 together with attached diffuser unit 13 is positioned on the bolts 20 and the wing nuts 21 are screwed tightly on the bolts 20 and exert pressure against the lid member 14. Power is then applied to motor 40 and the propeller 52 commences to turn.

The water in chamber 11 enters the intake opening 33 and is exhausted out of egress opening 72 by the action of propeller 52. As seen by the arrows in FIG. 2A, the water travels in a counter clockwise direction and a steady state momentum of the water throughout the chamber 11 is quickly obtained which conserves power in the motor 40 and more closely replicates actual environmental conditions. The blackout curtain 20 may be mounted around the chamber 11 to shut off light if respiration measurements are desired and may be removed such that ambient light conditions take place if combined respiration and production measurements are desired.

Such measurements may be obtained by determining the oxygen ($O_2$) or carbon dioxide ($CO_2$) levels in the chamber 11 and these measurements are taken by inserting an appropriate probe (not shown) which will replace rubber stopper 31. Samples of chamber water may be obtained from access port 24 or pollutants may be introduced through access port 24 to determine what significance their addition may have on the respiration and/or oxygen production of the substrate in the container 10.

Such measurements will occur at intervals over the desired period of time until the sampling period is completed. The unit is then removed from the operating position and, being readily portable, may be returned to the laboratory.

In the event there is a failure of the motor 40, the entire diffuser unit 13 may be quickly removed by removing wing nuts 43 and removing the diffuser unit 13 from the lid member 14. End diameter 63 is then removed and the entire mixing unit 50 will slide out of cylinder 44 to be easily replaced if necessary or repaired.

As stated earlier, the location of the access ports 23, 24 is of some importance. Access port 23, through which measurements such as oxygen or carbon dioxide content are made, is positioned such that the water in chamber 11 directly below the access port 23 is in a thoroughly mixed condition and that it is a relatively uniform flow because of its position removed from the diffuser unit 13 and, in particular, from the intake and exit openings 33, 72, respectively, at which points there may be flow dislocations because of the diffuser unit 13. Access port 24 is located close to intake opening 33 such that contaminants introduced at this point are speedily ingested by the diffuser unit 13 through intake opening 33 and diffused throughout the water in the metabolism container 10.

In operation to date, it has been found that a chamber 11 in the form of a cylinder having a diameter of 15" and a height of 8" is satisfactory for periodic measurements that may be taken over periods ranging from a few hours to several days. In such a unit, a D.C. motor 40 of 1.5–3.0 volts will provide the necessary power to propeller 52 to give a water velocity of approximately 20 cm/sec. which adequately may represent a natural flow condition. Such a motor can be operated with two size D batteries either in parallel or series configuration depending on the flow rate desired. In the series configuration, when the motor 40 runs at 3.0 volts, a life expectancy of approximately 4–6 hours with substantially uniform water velocity can be expected. The substrate should take up approximately half of the volume of the chamber 11 before the water is added. A container having a diameter of 10" with varying heights depending on the desired ratio of substrate to water is also contemplated to operate satisfactorily with the same characteristics as described above.

Various modifications are contemplated to the apparatus described. The chamber 11 may have a removable closure member 12 so that it can simply be pressed into the creek or river bottom over a suitable substrate for a predetermined distance. Such a technique even more clearly represents those conditions occurring naturally. Rather than a power source such as batteries, an alternator or generator could be used to generate power from the water moving past the metabolism container 10. Such a technique would eliminate the necessity of replacing batteries at regular intervals. In addition, while it is intended that the measuring probes are inserted intermittently to obtain the water characteristics, such probes may be inserted when the unit is placed in its operating position and continuously monitored from a remote location.

Yet another modification relates to the shape of the chamber 11. While it is desirable to have a cylindrical shape for the chamber 11, other shapes could be used which would retain the advantages of non-disruptive flow. Such shapes could include an oblong shape or others. All that is required is that the inner circumferential surfaces of the chamber be continuous to avoid flow dislocation such as would be the case in, for example, a rectangular or square container.

While, therefore, various specific embodiments of the apparatus have been described, such embodiments should be considered illustrative only and not as limiting the scope of the invention as defined in the accompanying claims.

I claim:

1. A portable and submersible metabolism container for ecological testing comprising a substantially air and water tight chamber having an upper area, a water diffuser means mounted in the upper area and within said chamber, a power source for said water diffuser means and access means to said chamber, said water diffuser means being operable to substantially uniformly propel said water within said chamber at a relatively constant velocity.

2. A metabolism container as in claim 1 wherein said chamber has substantially continuous inner circumferential walls.

3. A metabolism container as in claim 2 wherein said water diffuser means includes a mixing unit mounted within a cylinder, said cylinder having a water intake opening, a water egress opening, said mixing unit being wholly mounted within said cylinder.

4. A metabolism container as in claim 3 wherein said container is substantially transparent.

5. A metabolism container as in claim 4 and further comprising blackout means to darken substantially the entire exterior of said chamber.

6. A metabolism container as in claim 3 wherein said mixing unit comprises a motor coupled to a propeller and a source of elecrical energy for said motor, said motor and said propeller being mounted wholly within said cylinder.

7. A metabolism conainer as in claim 6 wherein said chamber includes a circumferential portion and a first and second closure member, each defining an end of said circumferential portion, one of said first and second lid portions being removably sealed to said circumferential portion, said diffuser unit being connected to said one lid portion and being removable therewith.

8. A metabolism container as in claim 7 wherein said diffuser unit is mounted on said one lid portion, said water intake opening of said cylinder being mounted upstream of said propeller and closely adjacent to the axis of said container.

9. A metabolism container as in claim 7 wherein said motor is a direct current motor and said source of electrical energy is a battery pack.

10. A metabolism container as in claim 9 wherein said cylinder lies on a diameter of said chamber, said water egress opening extending a distance along the periphery of said cylinder and being located downstream of said propeller.

11. A metabolism container as in claim 10 wherein said water intake opening extends a distance along the periphery of said cylinder on the opposite side of said cylinder from said water egress opening.

12. A metabolism container as in claim 11 wherein said water egress opening extends along said cylinder from a first larger area closest said propeller in decreasing cross-sectional area to a final exit area at the far end of said cylinder removed from said propeller.

13. Water diffuser apparatus comprising a cylinder, a propeller, and a power source for said propeller mounted within said cylinder, a water intake opening on the periphery of said cylinder adjacent to and upstream of said propeller and a water egress opening extending in a decreasing cross-sectional area along said periphery of said cylinder from a position adjacent to and downstream of said propeller to a position at the far end of said cylinder, said water egress opening being located on the opposite side of said cylinder from said water intake opening.

14. Water diffuser apparatus as in claim 13 wherein said water egress opening is a trapezoidal shaped opening extending in decreasing cross-sectional area from a larger area adjacent said propeller to a smaller area at the extended end of said cylinder.

* * * * *